United States Patent [19]
Horan et al.

[11] Patent Number: 6,024,454
[45] Date of Patent: Feb. 15, 2000

[54] MICROSCOPE DRAPE SYSTEM

[75] Inventors: Robert T. Horan; Phyllis J Horan, both of Fountain Hills, Ariz.

[73] Assignee: PH Medical, Inc., Fountain Hills, Ark.

[21] Appl. No.: 09/206,003

[22] Filed: Dec. 4, 1998

[51] Int. Cl.⁷ .............................. G03B 11/04; B65D 85/38
[52] U.S. Cl. ........................ 359/510; 359/511; 359/513; 206/316.1
[58] Field of Search .................................... 359/510, 511, 359/512, 513, 514, 368, 372; 206/305, 316.1, 316.2, 316.3

[56] References Cited

U.S. PATENT DOCUMENTS

| | | | |
|---|---|---|---|
| 3,528,720 | 9/1970 | Treace | 359/510 |
| 3,698,791 | 10/1972 | Walchle et al. | 359/510 |
| 4,266,663 | 5/1981 | Geraci | 359/510 |
| 4,385,812 | 5/1983 | Willie et al. | 359/511 |
| 4,564,270 | 1/1986 | Willie | 359/511 |
| 5,155,624 | 10/1992 | Flagler | 359/510 |
| 5,311,358 | 5/1994 | Pederson et al. | |
| 5,467,223 | 11/1995 | Cleveland, Jr. et al. | 359/510 |
| 5,608,574 | 3/1997 | Heinrich | 359/510 |

OTHER PUBLICATIONS

Brochure "Microscope Laser Drapes", Microtek Medical, Inc. 1991, 8 pages.

*Primary Examiner*—Ricky D. Shafer
*Attorney, Agent, or Firm*—Lyon & Lyon LLP

[57] ABSTRACT

A sterile drape system for a surgical microscope includes an adapter ring which is attached around the outside diameter of the objective lens of the microscope, to provide a standard or uniform outside diameter mounting surface. A drape lens is contained within a drape ring. A sterile drape is attached to the drape ring. The drape ring is frictionally engaged onto the outside diameter of the adapter ring and the drape pulled over the microscope. A lens ring having a primary lens is attached to the drape ring with a quick disconnect fitting. The sterile drape system eliminates the need to inventory multiple surgical microscope drapes and reduces waste resulting from the selection of a drape not matching the surgical microscope to be used.

11 Claims, 4 Drawing Sheets

MICROSCOPE DRAPE SYSTEM

BACKGROUND OF THE INVENTION

The field of the invention is sterile drapes for surgical microscopes.

Microscopes are often used in surgical procedures. In many of these procedures, such as neuro surgery and plastic surgery, the surgeon must manipulate exceptionally small blood vessels, nerve bundles, muscles, nerves and other tissue. These procedures require viewing the surgical site through a surgical microscope, so that the fine details in the surgical site can be clearly seen by the surgeon.

The area around the surgical site must be maintained sterile. As it is difficult or impossible to sterilize the surgical microscope, it is common practice to cover the microscope with a sterile drape. However, the sterile drape must not interfere with the view of the surgical site through the objective lens of the microscope. Accordingly, devices have been provided to allow surgical microscopes to be covered with a sterile drape, while not interfering with the objective lens. For example, Pederson et al., U.S. Pat. No. 5,311,358, discloses a universal microscope drape having an adapter ring with the ring fitting between the objective lens and the rest of the microscope. The objective lens must be removed to install the adapter ring.

However, various disadvantages have been realized in trying to adapt sterile drapes to surgical microscopes. One disadvantage arises because most hospitals have two or more different types of surgical microscopes. As the dimensions of the objective lenses of different microscopes have different dimensions, sterile drapes having different drape rings must be supplied and stored at the hospital. Consequently, the logistics of setting up the operating room before surgery are more complicated, as the correct surgical drape must be selected to match the particular microscope in that operating room. If the incorrect drape is selected, the operation will be delayed while the correct drape is identified, located and installed. The opened incorrect drape is then necessarily discarded and wasted. In addition, the outside diameters of the objective lens on several surgical microscopes can be so near to each other that an incorrect drape could be inadvertently placed onto a microscope which it is not designed to properly fit. As a result, the sterile barrier function of the drape may not be fully realized.

Another disadvantage in draping surgical microscopes is that with some drapes, the mounting ring has an injection molded lens, which can cause distortion. As a result, some surgeons will simply discard the plastic lens. When this occurs, the contaminated objective lens of the surgical microscope itself is exposed to blood, and other fluids, so that frequent cleaning may be required. This exposure and cleaning of the objective lens increases the potential for scratching or damage to the objective lens, an expensive component of the surgical microscope.

Where surgical drapes have mounting rings or adapters which fit between the objective lens and the other lenses in the surgical microscope, the distance between the lenses may be changed, thereby changing the focusing characteristics of the microscope. Accordingly, there remains a need for a sterile drape for a surgical microscope which provides a sterile barrier without changing the focal length of the microscope.

SUMMARY OF THE INVENTION

To these ends, a method for providing a sterile barrier over a surgical microscope includes placing an adapter ring over the objective lens of the microscope, without removing the objective lens from the microscope. A drape ring unit is preferably slidably engaged onto the adapter ring. A sterile drape attached to the drape ring unit is unfurled and pulled up and around the microscope.

A sterile drape system for a surgical microscope advantageously includes an adapter ring placed around the objective lens of the microscope. A drape ring unit preferably has a sterile drape attached to the drape ring. An optional drape lens is provided within the drape ring. The drape ring has an inside diameter dimensioned to slidably fit over the outside diameter of the adapter ring. A lens ring having the primary lens is provided.

Other and further objects and advantages will appear hereinafter.

DETAILED DESCRIPTION OF THE PREFERRED EMBODIMENT

Figure 1:
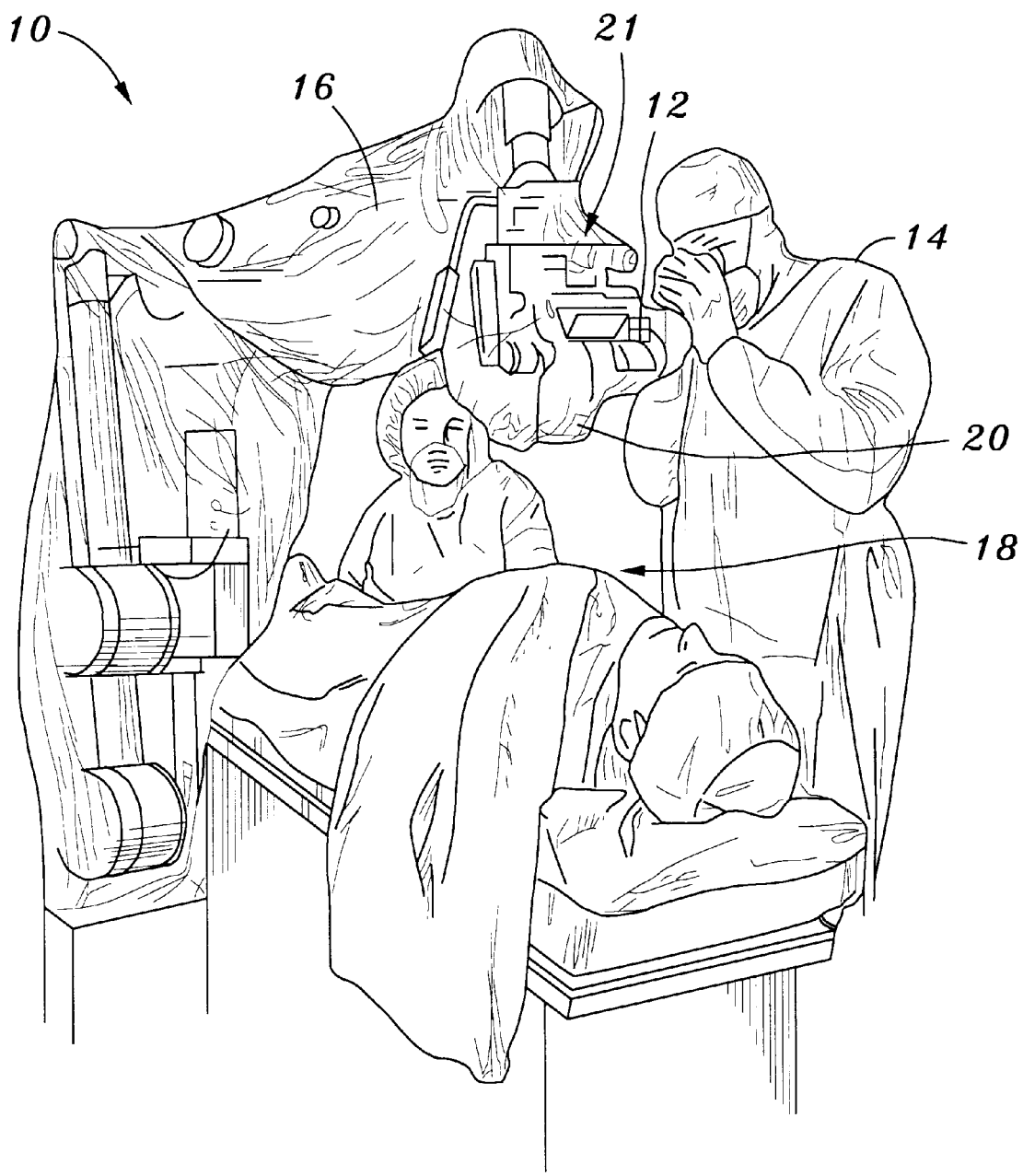
FIG. 1 is a perspective view of the present invention in use in an operating room.

Turning now in detail to the drawings, as shown in FIG. 1, a surgical microscope 12 is used by a surgeon 14 in an operating room 10. The microscope 12 is covered with a sterile drape system 21 having a drape 16 which forms a sterile barrier between the non-sterile microscope 12 and its supporting arm, and the sterile field 18 around the surgical site. The microscope 12 has an objective lens 20 positioned directly over and adjacent to the surgical site.

Figure 2:
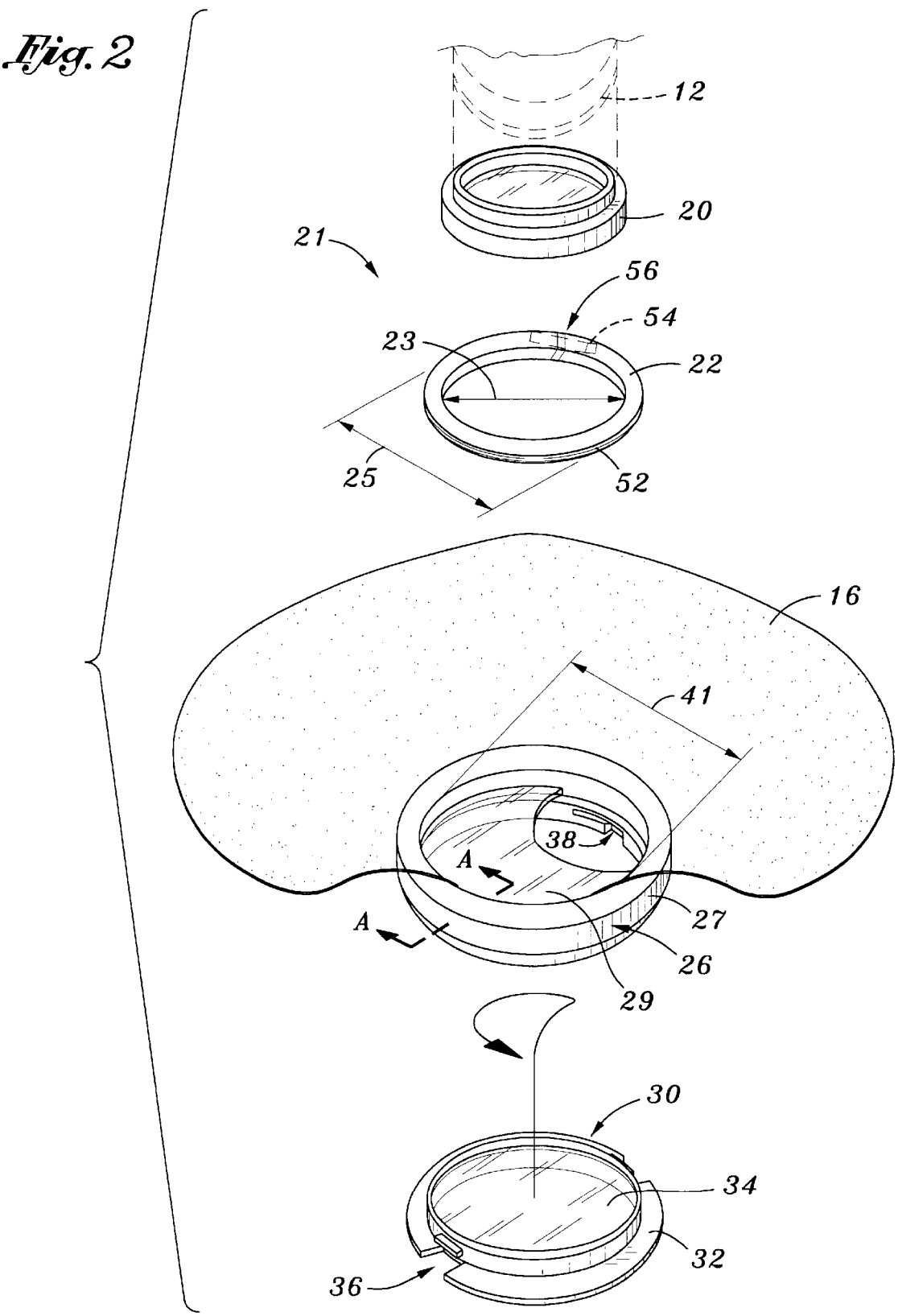
FIG. 2 is an exploded perspective view of the invention.
Figure 3:
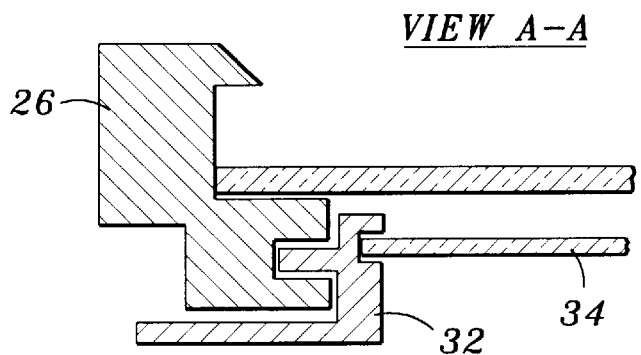
FIG. 3 is a partial section view taken along line A—A of FIG. 2.
Figure 6:
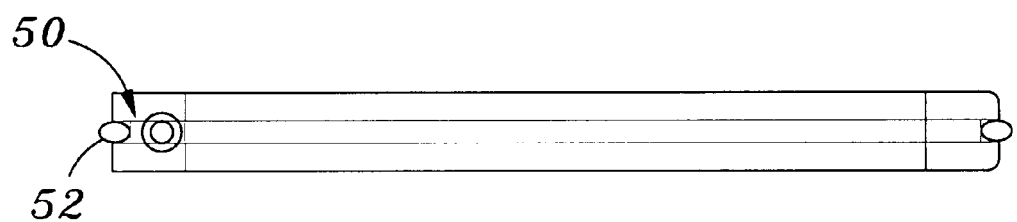
FIG. 6 is a side view of the adapter ring shown in FIG. 2.

Turning to FIG. 2, the present sterile drape system 21 includes an adapter ring 22, having an inside diameter 23 large enough to fit over the objective lens 20 of all commonly used surgical microscopes. Referring momentarily to FIGS. 2 and 6, the adapter ring 22 has a circumferential groove 50 which accommodates a resilient O-ring 52. The O-ring 52 projects slightly beyond the perimeter of the adapter ring 22. An additional O-ring may be used on the inside of the adapter to accommodate minor out of round diameter tolerance of the objective lens. A clamp screw 54 is threaded into the adapter ring 22 and extends across the gap or opening 56. The head of the clamp screw 54 is accessed by temporarily pulling the O-ring away from the groove 50. Various equivalents to the adapter ring 22 may also be used, such as split rings which can be temporarily spread apart and then clamped onto the objective lens 20, clamp fittings, two piece clamping designs, radial set screws, etc.

Figure 4:
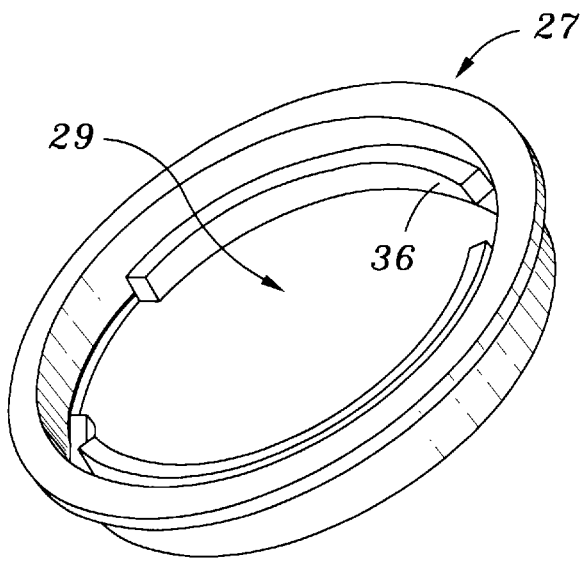
FIG. 4 is a perspective view of the drape ring shown in FIG. 2, detached from the drape.

Referring to FIGS. 2 and 4, a drape ring unit 26 has a drape ring 27. The inside diameter 41 of the drape ring 27 is dimensioned to slide over and fit onto the outside diameter 25 of the O-ring 52 on the adapter ring 22. A sterile drape 16 is permanently attached to the top side, or bottom surface of the drape ring 27. An optional transparent drape lens 29 is secured within the drape ring 27. The e.g., heat sealed attachment and fit of the drape lens 29 and drape 16 to the drape ring 27 are sufficiently continuous to maintain a sterile barrier from one side to the other. A quick release fitting, such as a bayonet fitting 36 is provided on the bottom end of the drape ring 27.

Figure 5:
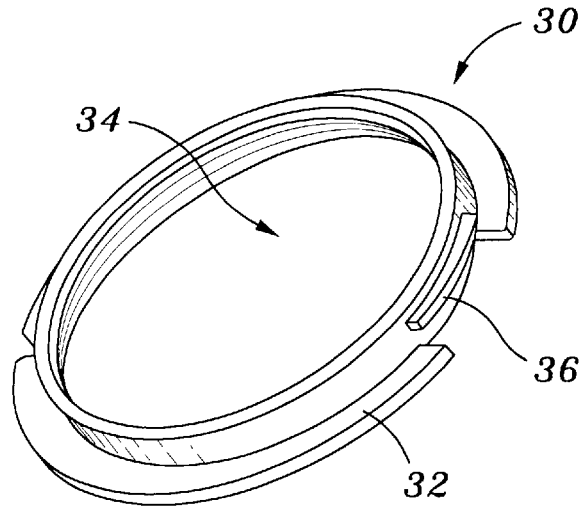
FIG. 5 is a perspective view of the lens ring shown in FIG. 2.

Referring to FIGS. 2 and 5, a primary lens unit 30 includes a lens ring 32 containing a primary lens 34. The lens ring 32 includes a bayonet fitting 36 adapted to quickly engage and disengage the bayonet fitting 36 on the drape ring 27. The lenses 29 and 34 are preferably impact resistant glass, although other materials such as clear plastic may be used. The lenses 29 and 34 are flat or curved windows and do not affect the image seen through the microscope.

In use, the adapter ring 22 is placed around the objective lens 20 of the surgical microscope 12. The O-ring is pulled out or away from the groove 50 to expose the head of the clamp screw 54. The clamp screw 54 is turned with a hand tool to clamp the adapter ring 22 onto the objective lens 20. The O-ring 52 is released and snaps back into the groove 50. Next, the drape ring unit 26 is removed from its package and the drape ring 27 is pushed over and onto the outside diameter 25 of the O-ring 52 on the adapter ring 22. The friction fit between the inside diameter 41 of the drape ring 27 and the O-ring 52 on the adapter ring 22 attaches them together. The resilient O-ring accommodate minor out-of-round or diameter tolerances. The drape lens 29 in the drape unit 26 is concentric and aligned with the objective lens 20. The drape 16 is unfurled and pulled up and over the microscope 12 and its supporting arm, as shown in FIG. 1.

The surgeon 14 can then view the surgical site using the microscope 12 through the objective lens and the optional drape lens 29. During the operation, the drape ring 27, drape 16, and drape lens 29, when used, form a sterile barrier, to separate the microscope 12 and supporting arm from the surgical site. The objective lens 20 is never removed from the microscope 12, thereby simplifying installation, reducing risk of damage to the microscope 12 or objective lens 20, and avoiding any changes in focusing characteristics resulting from a change in the spacing between the objective lens 20 and other lenses within the microscope 12.

At the conclusion of the surgical procedure, the drape ring 27 is pulled off of the adapter ring 22, and preferably discarded along with the now contaminated drape 16. The adapter ring 22 is preferably left on the objective lens 20, as regardless of the outside diameter of the objective lens 20, the outside diameter of the adapter ring 22, which is now the mating surface for the drape ring 27, remains unchanged. In this way, with an adapter ring 22 installed on the objective lens 20 of the every microscope 12 in a hospital, only a single drape ring unit 26 need be inventoried at the hospital. Accordingly, procurement, storage and use of the sterile drape for a surgical microscope are simplified. Multiple adapter rings, having a uniform outside (O-ring) diameter, and having varying nominal inside diameters, for accommodating different objective lenses, may be used.

In certain operations, the optional drape lens 29 will be splattered with blood or other fluids, thereby obscuring the surgeon's vision through the microscope 12. Since the drape lens 29 (and the entire drape ring unit 26) cannot be removed during the operation (while maintaining the sterile barrier), the drape lens 29 must be cleaned while in place. Cleaning this downward facing glass surface may be difficult, especially if the microscope is still positioned over the surgical site. To avoid this disadvantage, the lens 34 in the ring 32 may be removed for cleaning while the sterile barrier is maintained by the optional drape lens 29. In use, the lens ring 32 is attached concentrically onto the drape ring 27 via the bayonet fitting 36 on the lens ring 32 engaging the corresponding fitting 38 on the drape ring 27. The primary lens 34 in the lens ring 32 prevents any splatter from reaching the drape lens 29. When the second lens 34 becomes splattered with e.g., blood, the lens ring 32 can be quickly removed and cleaned, away from the surgical site, and then quickly and easily reinstalled. Removal of the lens ring 32 for cleaning does not break the sterile field, as the sterile barrier is provided by the drape ring unit 26. In addition, the operation can proceed while the primary lens 34 in the lens ring is being cleaned.

To maintain the sterile barrier, either the drape lens 29 or the primary lens 34 must be in place at all times. The greatest flexibility is provided when both are used. However, some surgeons may prefer to use only the drape lens 29, or only the primary lens 34, or both of them together.

Thus, a novel, sterile drape system for a surgical microscope has been shown and described. It will be apparent that various modifications, substitutions, and uses of equivalents may be made, without departing from the spirit and scope of the invention. The invention, therefore, should not be limited, except by the following claims.

What is claimed is:

1. A sterile drape system for a surgical microscope having an objective lens, comprising:
   an adapter ring;
   a resilient element around an outside surface of the adapter ring;
   means for attaching the adapter ring to the objective lens; and
   a drape ring unit having a sterile drape attached to a drape ring and with the drape ring having an inside diameter dimensioned to engage onto the resilient element of the adapter ring.

2. The system of claim 1 wherein the means for attaching comprises a split ring and a clamp screw.

3. The system of claim 1 further comprising a drape lens within the drape ring.

4. The system of claim 1 further comprising a drape lens attached to the drape ring.

5. A sterile drape system kit for a surgical microscope having an objective lens, comprising:
   a plurality of adapter rings, with all of the rings having the same outside diameter and different inside diameters; and
   a drape ring unit having a sterile drape attached to a drape ring, and with the drape ring having an inside diameter dimensioned to fit onto the outside diameter of each adapter ring.

6. A sterile drape system for a surgical microscope having an objective lens, comprising:
   an adapter ring;
   means for attaching the adapter ring to the objective lens;
   a drape ring unit having a sterile drape attached to a drape ring and with the drape ring having an inside diameter dimensioned to engage onto the adapter ring;
   a lens ring housing engageable onto the drape ring; and
   a primary lens attached to the lens ring housing.

7. The sterile drape system of claim 6 wherein the lens ring housing is attached to the drape ring with a quick disconnect fitting.

8. The sterile drape system of claim 7 wherein the quick disconnect fitting is a bayonet fitting.

9. A drape system for a surgical microscope having an objective lens, comprising:

an split adapter ring;

a fastener threaded into the split adapter ring for clamping the split adapter ring onto the objective lens; and a drape ring unit including a drape attached to a drape ring and with the drape ring having an inside diameter dimensioned to slide over the split adapter ring.

10. The system of claim 9 further comprising a drape lens in the drape ring.

11. The system of claim 10 further comprising a primary lens unit attachable onto the drape ring unit, and a primary lens in the primary lens unit.

* * * * *